United States Patent
Fukuda et al.

(10) Patent No.: US 10,071,378 B2
(45) Date of Patent: Sep. 11, 2018

(54) MICROCHANNEL DEVICE AND METHOD PERTAINING THERETO

(71) Applicant: UNIVERSITY OF TSUKUBA, Tsukubu-shi, Ibaraki (JP)

(72) Inventors: Junji Fukuda, Tsukuba (JP); Hiroaki Suzuki, Tsukaba (JP); Anna Yamagishi, Tsukuba (JP); Junko Enomoto, Tsukuba (JP); Masatoshi Yokokawa, Tsukuba (JP)

(73) Assignee: UNIVERSITY OF TSUKUBA, Ibaraki (JP)

( * ) Notice: Subject to any disclaimer, the term of this patent is extended or adjusted under 35 U.S.C. 154(b) by 10 days.

(21) Appl. No.: 14/775,285

(22) PCT Filed: Feb. 24, 2014

(86) PCT No.: PCT/JP2014/054299
§ 371 (c)(1),
(2) Date: Sep. 11, 2015

(87) PCT Pub. No.: WO2014/141861
PCT Pub. Date: Sep. 18, 2014

(65) Prior Publication Data
US 2016/0024451 A1    Jan. 28, 2016

(30) Foreign Application Priority Data

Mar. 13, 2013  (JP) .................................. 2013-050756

(51) Int. Cl.
| | | |
|---|---|---|
| *B01L 3/00* | (2006.01) | |
| *B01F 5/00* | (2006.01) | |
| *B01F 13/00* | (2006.01) | |
| *B01F 3/08* | (2006.01) | |
| *B01L 3/02* | (2006.01) | |
| *G01N 1/38* | (2006.01) | |
| *C12M 3/06* | (2006.01) | |

(52) U.S. Cl.
CPC ...... *B01L 3/502784* (2013.01); *B01F 3/0803* (2013.01); *B01F 5/0085* (2013.01); *B01F 13/0061* (2013.01); *B01F 13/0069* (2013.01); *B01F 13/0071* (2013.01); *B01F 13/0072* (2013.01); *B01L 3/0293* (2013.01); *B01L 3/5027* (2013.01); *B01L 3/502792* (2013.01); *C12M 23/16* (2013.01); *G01N 1/38* (2013.01); *B01L 2200/0605* (2013.01); *B01L 2300/088* (2013.01)

(58) Field of Classification Search
CPC ... C12M 23/16; B01F 3/0803; B01F 13/0061; B01F 13/0069; B01F 13/0071; B01F 13/0072; B01F 5/0085; B01F 5/064; B01F 5/0644; B01F 5/0645; B01F 5/0646; B01F 5/0647; B01L 3/5027; B01L 3/502769; B01L 3/502784; B01L 3/502792; B01L 3/0293; B01L 2200/0605; B01L 2300/088; G01N 1/38

See application file for complete search history.

(56) References Cited

U.S. PATENT DOCUMENTS

| | | | |
|---|---|---|---|
| 2006/0003439 A1* | 1/2006 | Ismagilov | B01F 5/0471 435/287.2 |
| 2013/0059322 A1 | 3/2013 | Hung et al. | |
| 2016/0215246 A1* | 7/2016 | Goh | C12M 23/16 |

FOREIGN PATENT DOCUMENTS

| | | |
|---|---|---|
| JP | 2004-147555 A | 5/2004 |
| JP | 2011-257238 A | 12/2011 |
| WO | 2011/014674 A2 | 2/2011 |

OTHER PUBLICATIONS

Niu, X et al. A microdroplet dilutor for high-throughput screening. Nature Chemistry. Jun. 2011. 3: 437-442.*
Fukuda, J et al. Processing of nanolitre liquid plugs for microfluidic cell-based assays. Science and Technology of Advanced Materials. 2012. 13: 064201 (7pp).*
Feb. 28, 2017 Office Action issued in Japanese Patent Application No. 2013-050756.
Sassa Fumihiro et al. "Microprocessing of Liquid Plugs for Bio/ chemical Analyses" Anal. Chem., 2008, vol. 80, pp. 6206-6213.
Sassa Fumihiro et al. "Coulometric Detection of Components in Liquid Plugs by Microfabricated Flow Channel and Electrode Structures" Anal. Chem., 2010, vol. 82, pp. 8725-8732.
May 27, 2014 International Search Report issued in International Patent Application No. PCT/JP2014/054299.

(Continued)

*Primary Examiner* — Renee Claytor
*Assistant Examiner* — Susan E. Fernandez
(74) *Attorney, Agent, or Firm* — Oliff PLC

(57) ABSTRACT

A microchannel device includes: an upstream channel portion configured to allow an upstream liquid plug and a gas to flow therethrough; a downstream channel portion configured to allow a downstream liquid plug and a gas to flow therethrough; a liquid holding portion provided between a downstream end portion of the upstream channel portion and an upstream end portion of the downstream channel portion, the liquid holding portion being configured to hold a main liquid plug therein; and a gas bypass channel portion provided so as to bypass the liquid holding portion from the downstream end portion of the upstream channel portion to the upstream end portion of the downstream channel portion, the gas bypass channel portion being configured to allow the gas to flow therethrough in a state in which the liquid holding portion holds the main liquid plug.

7 Claims, 9 Drawing Sheets

(56) References Cited

OTHER PUBLICATIONS

Nov. 11, 2016 Search Report issued in European Patent Application No. 14763586.6.

* cited by examiner

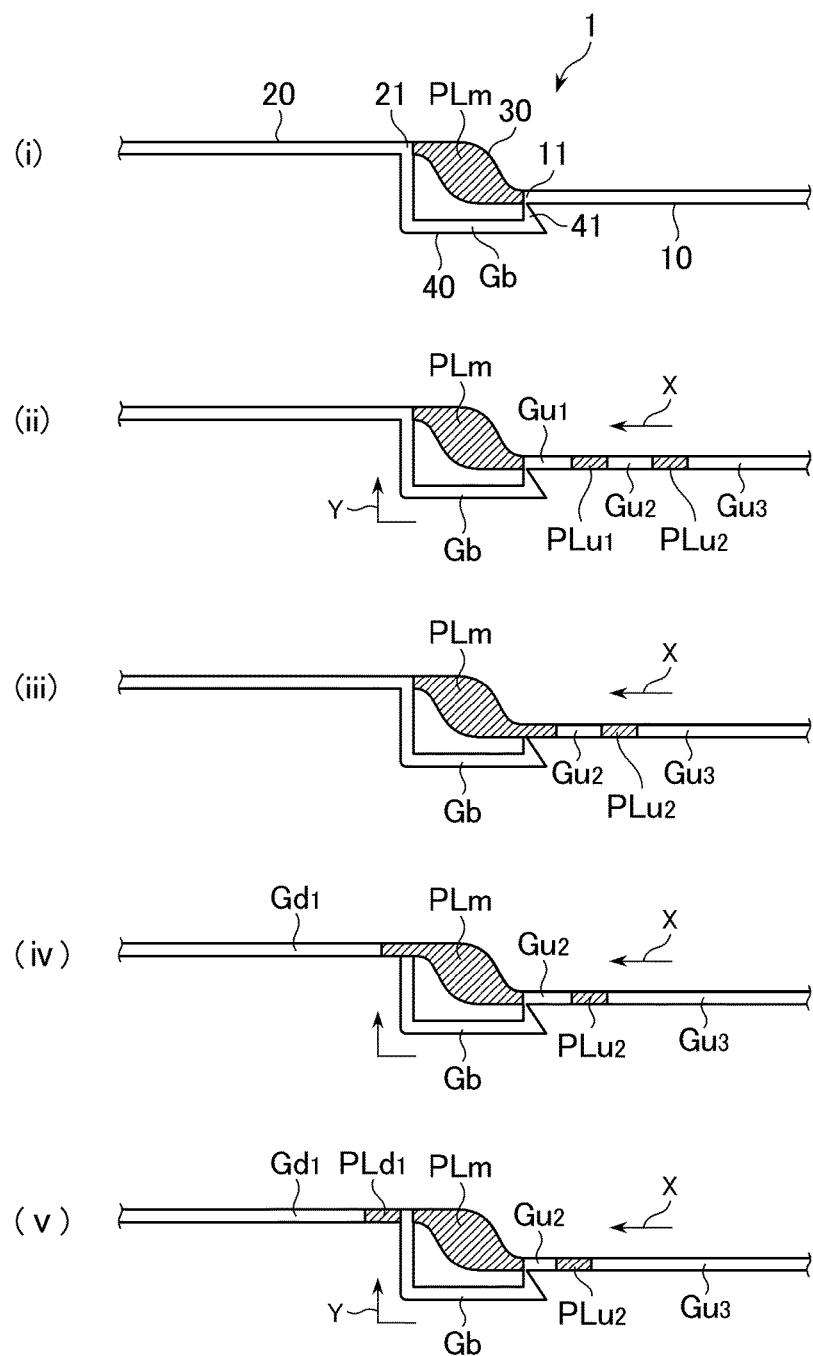

FIG.3B
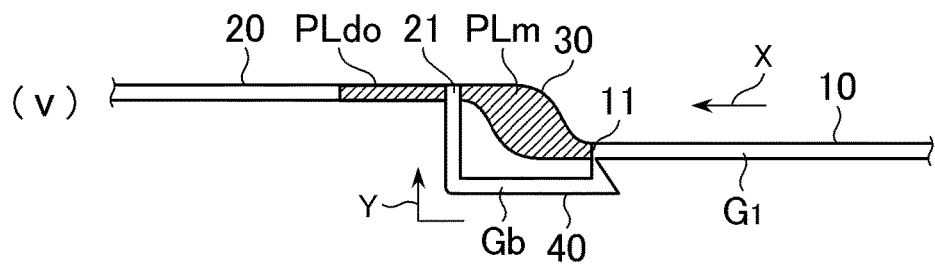
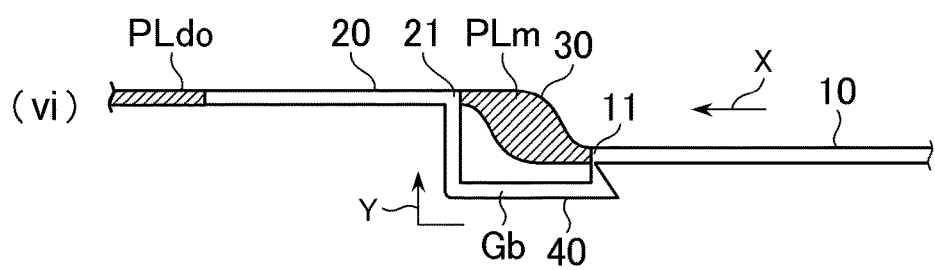
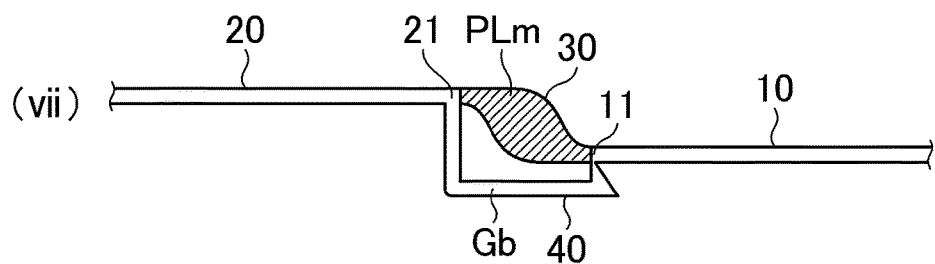

FIG.5
(i) 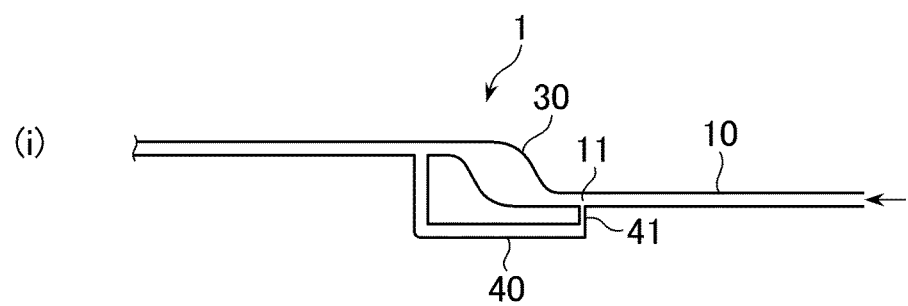
(ii) 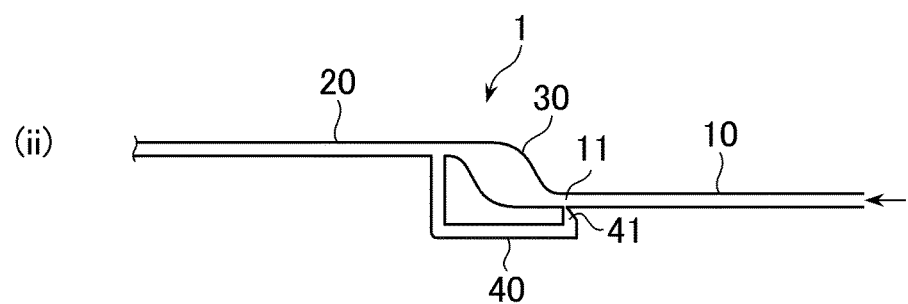
(iii) 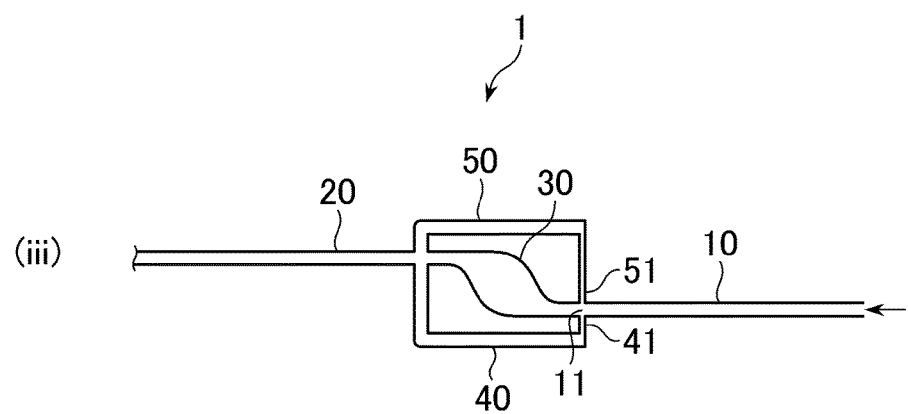

MICROCHANNEL DEVICE AND METHOD PERTAINING THERETO

TECHNICAL FIELD

The present invention relates to a microchannel device and a method relating thereto, and more particularly, to an effective manipulation of a tiny amount of liquid in the microchannel device.

BACKGROUND ART

Hitherto, for example, in Patent Literature 1, there is described a cell culture apparatus including at least two cell culture chambers stacked therein, each including a channel structure in which cells are firmly attached inside and that is perfused with a culture medium. Further, in Non Patent Literature 1 and Non Patent Literature 2, there is described technology for causing a liquid plug to flow through a channel of a microchannel device.

CITATION LIST

Patent Literature

[Patent Literature 1] JP 2004-147555 A

Non Patent Literature

[Non Patent Literature 1] Fumihiro Sassa et al., Anal. Chem. 2008, 80, 6206-6213
[Non Patent Literature 2] Fumihiro Sassa et al., Anal. Chem. 2010, 82, 8725-8732

SUMMARY OF INVENTION

Technical Problem

However, in the related-art microchannel devices, for example, it is difficult to change a cell culture environment in the culture medium over time (for example, to increase a concentration of a stimulating substance that stimulates a cell body (such as an animal cell and a microbe) in the culture medium in a stepwise manner) by adding the stimulating substance to the cell culture chamber while keeping a volume of the culture medium stored in the cell culture chamber constant.

Further, for example, in the related-art microchannel devices, in a case where the stimulating substance is brought into contact with the cell body cultured in a tiny amount of the culture medium in the cell culture chamber, it is difficult to efficiently sample apart of the tiny amount of the culture medium at short time intervals a plurality of times so as to evaluate a response of the cell body to the stimulating substance.

The present invention has been made to solve the above-mentioned problems, and one of the objects is to provide a microchannel device which achieves an effective manipulation of a tiny amount of liquid and a method relating thereto.

Solution to Problem

In order to solve the above-mentioned problems, according to one embodiment of the present invention, there is provided a method, including the following (a) to (g): (a) providing a microchannel device including an upstream channel portion, a downstream channel portion, a liquid holding portion provided between a downstream end portion of the upstream channel portion and an upstream end portion of the downstream channel portion, and a gas bypass channel portion provided so as to bypass the liquid holding portion from the downstream end portion of the upstream channel portion to the upstream end portion of the downstream channel portion; (b) filling the gas bypass channel portion with a gas and holding a main liquid plug in the liquid holding portion; (c) causing a first upstream liquid plug and a second upstream liquid plug to sequentially flow through the upstream channel portion toward the liquid holding portion; (d) causing the first upstream liquid plug to flow into the liquid holding portion to merge the first upstream liquid plug with the main liquid plug, and pushing out a part of the main liquid plug after the merging to the downstream channel portion; (e) causing a gas following the first upstream liquid plug to flow into the gas bypass channel portion to push out a part of the gas in the gas bypass channel portion to the upstream end portion of the downstream channel portion, to thereby cut the part of the main liquid plug, which is pushed out in the item (d), to form a first downstream liquid plug; (f) causing the second upstream liquid plug to flow into the liquid holding portion to merge the second upstream liquid plug with the main liquid plug and pushing out a part of the main liquid plug after the merging to the downstream channel portion; and (g) causing a gas following the second upstream liquid plug to flow into the gas bypass channel portion to push out a part of the gas in the gas bypass channel portion to the upstream end portion of the downstream channel portion, to thereby cut the part of the main liquid plug, which is pushed out in the item (f), to form a second downstream liquid plug. According to the one embodiment of the present invention, it is possible to provide the method capable of realizing an effective manipulation of a tiny amount of liquid in the microchannel device.

The method may further include the following (h): (h) recovering the first downstream liquid plug and the second downstream liquid plug. The item (c) may include causing the first upstream liquid plug and the second liquid plug to flow so that the second downstream liquid plug is formed in the item (g) within a time shorter than 1 second after the formation of the first downstream liquid plug in the item (e). The item (c) may include causing the first upstream liquid plug and the second liquid plug to flow so that the second upstream liquid plug is merged with the main liquid plug in the item (f) within a time shorter than 1 second after the first upstream liquid plug is merged with the main liquid plug in the item (d). A volume of each of the first upstream liquid plug, the second upstream liquid plug, the first downstream liquid plug, and the second downstream liquid plug, may be smaller than 1 μL.

The main liquid plug held in the liquid holding portion in the item (b) may contain a first factor, and one or both of the first upstream liquid plug and the second upstream liquid plug that are caused to flow through the upstream channel portion in the item (c) may contain a second factor which acts on the first factor. In this case, the first factor may be a cell body, and the second factor may be a substance which acts on the cell body.

In order to solve the above-mentioned problems, according to one embodiment of the present invention, there is provided a microchannel device, including: an upstream channel portion configured to allow an upstream liquid plug and a gas to flow therethrough; a downstream channel portion configured to allow a downstream liquid plug and a gas to flow therethrough; a liquid holding portion provided between a downstream end portion of the upstream channel portion and an upstream end portion of the downstream channel portion, the liquid holding portion being configured to hold a main liquid plug therein; and a gas bypass channel portion provided so as to bypass the liquid holding portion from the downstream end portion of the upstream channel portion to the upstream end portion of the downstream channel portion, the gas bypass channel portion being configured to allow the gas to flow therethrough in a state in which the liquid holding portion holds the main liquid plug. According to the one embodiment of the present invention, it is possible to provide the microchannel device capable of realizing an effective manipulation of a tiny amount of liquid.

In the microchannel device, the upstream channel portion, the liquid holding portion, and the gas bypass channel portion may be provided so that the upstream liquid plug flowing through the upstream channel portion toward the liquid holding portion holding the main liquid plug therein flows into the liquid holding portion without flowing into the gas bypass channel portion, and so that the gas flowing through the upstream channel portion toward the liquid holding portion holding the main liquid plug therein flows into the gas bypass channel portion without flowing into the liquid holding portion.

In the microchannel device, the upstream channel portion, the liquid holding portion, and the gas bypass channel portion may be provided so that a change in free energy caused when the upstream liquid plug flows from the upstream channel portion into the gas bypass channel portion becomes larger than a change in free energy caused when the upstream liquid plug flows from the upstream channel portion into the liquid holding portion in a state in which the gas bypass channel portion is filled with the gas and the main liquid plug is held in the liquid holding portion.

Advantageous Effects of Invention

According to the one embodiment of the present invention, the microchannel device which achieves an effective manipulation of a tiny amount of liquid and the method relating thereto are provided.

BRIEF DESCRIPTION OF DRAWINGS

FIG. 2A is an explanatory view for illustrating a part of a manipulation involved in an example of a method according to the embodiment of the present invention.

FIG. 3B is an explanatory view for illustrating another part of the manipulation involved in the other example of the method according to the embodiment of the present invention.

FIG. 5 is an explanatory view for illustrating still another example of the microchannel device according to the embodiment of the present invention.

DESCRIPTION OF EMBODIMENT

An embodiment of the present invention will be described below. It should be noted that the present invention is not limited to examples shown in this embodiment.

Figure 1:
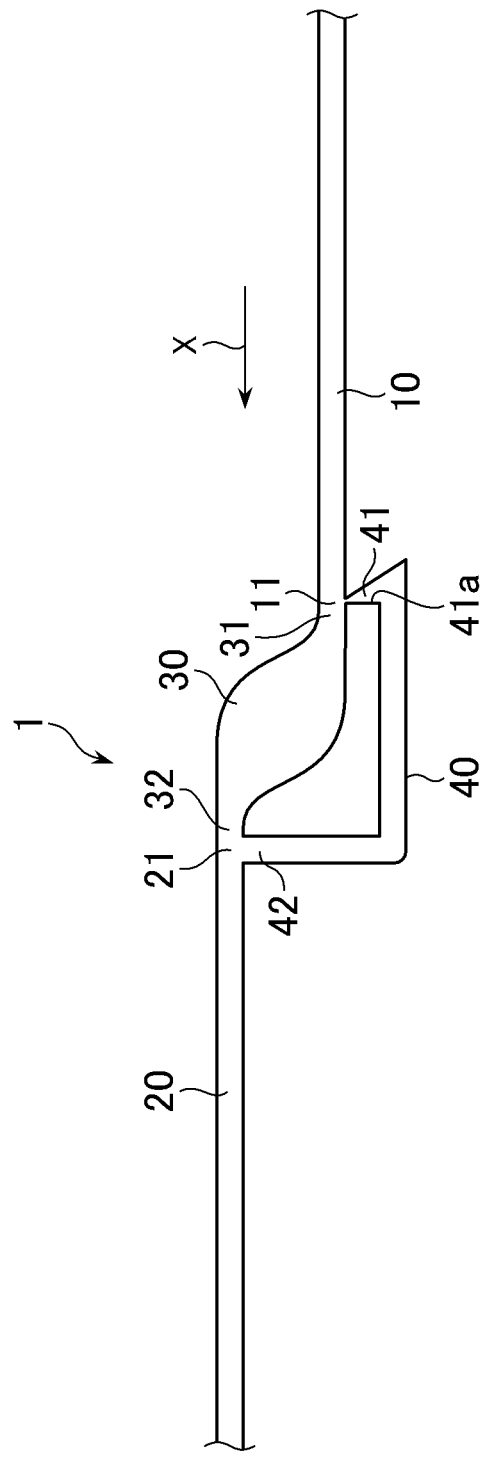
FIG. 1 is an explanatory view for illustrating an example of a microchannel device according to an embodiment of the present invention.
Figure 2B:
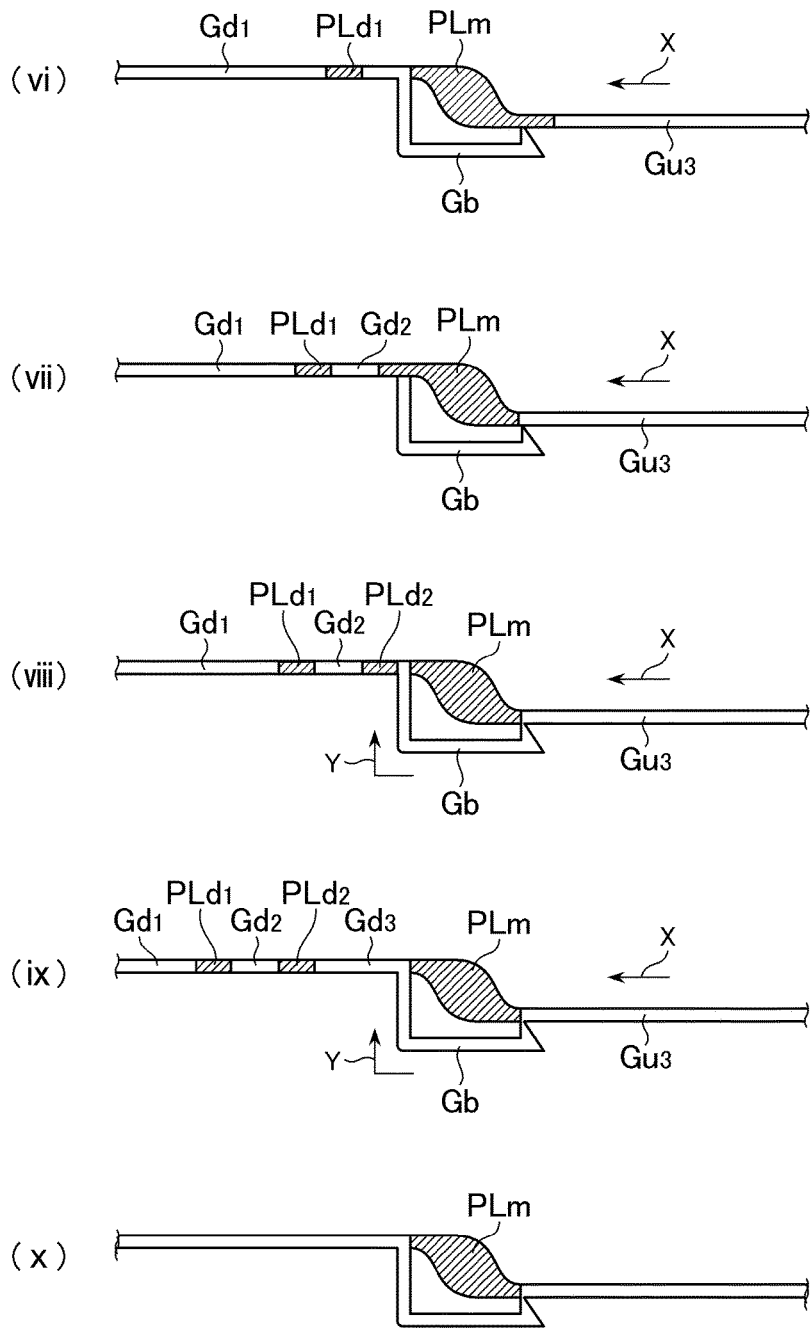
FIG. 2B is an explanatory view for illustrating another part of the manipulation involved in the example of the method according to the embodiment of the present invention.

In FIG. 1, an example of a microchannel device 1 according to this embodiment (hereinafter referred to as "the device 1") is illustrated. In FIG. 2A and FIG. 2B, a manipulation involved in an example of a method according to this embodiment (hereinafter referred to as "the method") is illustrated.

The device 1 includes, as illustrated in FIG. 1, FIG. 2A, and FIG. 2B: an upstream channel portion 10 configured to allow upstream liquid plugs PLu1 and PLu2 and gases Gu1, Gu2, and Gu3 to flow therethrough; a downstream channel portion 20 configured to allow downstream liquid plugs PLd1 and PLd2 and gases Gd1, Gd2, and Gd3 to flow therethrough; a liquid holding portion 30 provided between a downstream end portion 11 of the upstream channel portion 10 and an upstream end portion 21 of the downstream channel portion 20, the liquid holding portion being configured to hold a main liquid plug PLm therein; and a gas bypass channel portion 40 provided so as to bypass the liquid holding portion 30 from the downstream end portion 11 of the upstream channel portion 10 to the upstream end portion 21 of the downstream channel portion 20, the gas bypass channel portion being configured to allow a gas Gb to flow therethrough in a state in which the liquid holding portion 30 holds the main liquid plug PLm therein.

The method includes, as illustrated in FIG. 2A and FIG. 2B, the following (a) to (g): (a) providing the microchannel device (the device 1) including the upstream channel portion 10, the downstream channel portion 20, the liquid holding portion 30 provided between the downstream end portion 11 of the upstream channel portion 10 and the upstream end portion 21 of the downstream channel portion 20, and the gas bypass channel portion 40 provided so as to bypass the liquid holding portion 30 from the downstream end portion 11 of the upstream channel portion 10 to the upstream end portion 21 of the downstream channel portion 20; (b) filling the gas bypass channel portion 40 with the gas Gb and holding the main liquid plug PLm in the liquid holding portion 30; (c) causing the first upstream liquid plug PLu1 and the second upstream liquid plug PLu2 to sequentially flow through the upstream channel portion 10 toward the liquid holding portion 30; (d) causing the first upstream liquid plug PLu1 to flow into the liquid holding portion 30 to merge the first upstream liquid plug PLu1 with the main liquid plug PLm and pushing out a part of the main liquid plug PLm after the merging to the downstream channel portion 20; (e) causing the gas Gu2 following the first upstream liquid plug PLu1 to flow into the gas bypass channel portion 40 to push out a part of the gas Gb in the gas bypass channel portion 40 to the upstream end portion 21 of the downstream channel portion 20, to thereby cut the part of the main liquid plug PLm, which is pushed out in the item (d), to form the first downstream liquid plug PLd1; (f) causing the second upstream liquid plug PLu2 to flow into the liquid holding portion 30 to merge the second upstream liquid plug PLu2 with the main liquid plug PLm and pushing out a part of the main liquid plug PLm after the merging to the downstream channel portion 20; and (g) causing the gas Gu3 following the second upstream liquid plug PLu2 to flow into the gas bypass channel portion 40 to push out a part of the gas Gb in the gas bypass channel portion 40 to the upstream end portion 21 of the downstream channel portion 20, to thereby cut the part of the main liquid plug PLm, which is pushed out in the item (f), to form the second downstream liquid plug PLd2.

In FIG. 1, FIG. 2A, and FIG. 2B, a direction indicated by the arrow X is a direction in which the liquids and the gases flow in the device 1 (the same applies to the other drawings). Specifically, the direction indicated by the arrow X is a downstream direction, whereas a direction opposite to the direction indicated by the arrow X is an upstream direction. The arrow Y illustrated in FIG. 2A and FIG. 2B indicates a flow of the gas in the gas bypass channel portion 40 (the same applies to the other drawings).

In the above-mentioned item (a) of the method, the device 1 is provided. The upstream channel portion 10 of the device 1 is a channel through which the upstream liquid plugs PLu1 and PLu2 that is caused to flow into the liquid holding portion 30, and the gases Gu1, Gu2, and Gu3 that is caused to flow into the gas bypass channel portion 40, flow.

The upstream channel portion 10 is provided upstream of the liquid holding portion 30, and is connected to the liquid holding portion 30 at the downstream end portion 11. At the downstream end portion 11 of the upstream channel portion 10, an upstream end portion 41 of the gas bypass channel portion 40 is open.

The downstream channel portion 20 is a channel through which the downstream liquid plugs PLd1 and PLd2 formed from the main liquid plug PLm held in the liquid holding portion 30, and the gases Gd1, Gd2, and Gd3 flowing out of the gas bypass channel portion 40, flow.

The downstream channel portion 20 is provided downstream of the liquid holding portion 30, and is connected to the liquid holding portion 30 at the upstream end portion 21. At the upstream end portion 21 of the downstream channel portion 20, a downstream end portion 42 of the gas bypass channel portion 40 is open.

The liquid holding portion 30 is provided between the upstream channel portion 10 and the downstream channel portion 20. Specifically, the liquid holding portion 30 is provided between the downstream end portion 11 of the upstream channel portion 10 and the upstream end portion 21 of the downstream channel portion 20.

More specifically, the liquid holding portion 30 is provided downstream of the upstream end portion 41 of the gas bypass channel portion 40 (more specifically, an opening of the upstream end portion 41 of the gas bypass channel portion 40, which is located at the downstream end portion 11 of the upstream channel portion 10), the upstream end portion 41 being connected to the downstream end portion 11 of the upstream channel portion 10, and is provided upstream of the downstream end portion 42 of the gas bypass channel portion (more specifically, an opening of the downstream end portion 42 of the gas bypass channel portion 40, which is located at the upstream end portion 21 of the downstream channel portion 20), the downstream end portion 42 being connected to the upstream end portion 21 of the downstream channel portion 20. The liquid holding portion 30 is also referred to as an intermediate channel that connects the upstream channel portion 10 and the downstream channel portion 20 in a main channel including the upstream channel portion 10 and the downstream channel portion 20.

A shape of the liquid holding portion 30 is not particularly limited. For example, as illustrated in FIG. 1, FIG. 2A, and FIG. 2B, a sectional area of at least a part thereof may be larger than a sectional area of the downstream end portion 11 of the upstream channel portion 10 and a sectional area of the upstream end portion 21 of the downstream channel portion 20.

The gas bypass channel portion 40 is a channel to allow the gas flowing through the upstream channel portion 10 to flow into the downstream channel portion 30 without allowing the gas to flow into the liquid holding portion 30 in a state in which the liquid holding portion 30 holds the main liquid plug PLm.

Specifically, the gas bypass channel portion 40 is a channel to allow the gas flowing through the upstream channel portion 10 to bypass the liquid holding portion 30 to guide the gas to the downstream channel portion 20 in a state in which the liquid holding portion 30 holds the main liquid plug PLm. Therefore, in contrast to the upstream channel portion 10 and the downstream channel portion 20, the liquid does not flow through the gas bypass channel portion 40.

Further, from the above-mentioned item (c) to the above-mentioned item (g), the gas bypass channel portion 40 may be hermetically closed except that the upstream end portion 41 is open to the downstream end portion 11 of the upstream channel portion 20 and the downstream end portion 42 is open to the upstream end portion 21 of the downstream channel portion 20. Specifically, in this case, from the above-mentioned item (c) to the above-mentioned item (g), the gas Gb does not flow in the gas bypass channel portion 40 except for the flow of the gas Gb from the upstream end portion 41 to the downstream end portion 42.

The gas bypass channel portion 40 may be provided, as in the example illustrated in FIG. 1, FIG. 2A, and FIG. 2B, so as not to have an opening other than at the upstream end portion 41 and the downstream end portion 42. However, the gas bypass channel portion 40 is not limited thereto. For example, although another opening(s) is formed in addition to the openings at the upstream end portion 41 and the downstream end portion 42, the other opening (s) is closed in the above-mentioned item (c) to the above-mentioned item (g).

Further, in the example illustrated in FIG. 1, FIG. 2A, and FIG. 2B, the gas bypass channel portion 40 includes the upstream end portion 41 that is an enlarged channel. Specifically, a sectional area of the upstream end portion 41 of the gas bypass channel portion 40 increases in a downstream direction of the gas bypass channel portion 40. Further, a sectional area of the opening of the upstream end portion 41 of the gas bypass channel portion 40, which is located at the downstream end portion 11 of the upstream channel portion 10, is smaller than a sectional area of the downstream end portion 11 of the upstream channel portion 10.

Further, in the example illustrated in FIG. 1, FIG. 2A, and FIG. 2B, the upstream end portion 41 of the gas bypass channel portion 40 extends from the downstream end portion 11 of the upstream channel portion 10 in a direction approximately orthogonal to a flow direction in the upstream channel portion 10.

A method of manufacturing the device 1 is not particularly limited as long as the method is for manufacturing the microchannel device including the upstream channel portion 10, the downstream channel portion 20, the liquid holding portion 30, and the gas bypass channel portion 40 described above. The device 1 may also include, for example, a substrate, the upstream channel portion 10, the downstream channel portion 20, the liquid holding portion 30, and the gas bypass channel portion 40, each of the portions being formed on a surface of the substrate as a groove.

In this case, a material that forms the substrate is not particularly limited, and may be, for example, a resin (for example, PDMS) or glass. The upstream channel portion 10, the downstream channel portion 20, the liquid holding portion 30, and the gas bypass channel portion 40 may be formed on the surface of the substrate by, for example, a microfabrication technology such as photolithography.

The device 1 is preferably used, in particular, to manipulate a tiny amount of liquid and gas. Specifically, a volume of the liquid holding portion 30 (specifically, a volume of the main liquid plug PLm held in the liquid holding portion 30) may be set to, for example, 0.1 µL to 1,000 µL, 0.1 µL to 500 µL, or 0.1 µL to 100 µL. Further, each of the sectional areas of the upstream channel portion 10, the downstream channel portion 20, and the gas bypass channel portion 40 may be set to, for example, 0.01 mm² to 1.0 mm², or 0.01 mm² to 0.1 mm².

In the device 1, the upstream channel portion 10, the liquid holding portion 30, and the gas bypass channel portion 40 may be provided so that the upstream liquid plugs PLu1 and PLu2 flowing through the upstream channel portion 10 toward the liquid holding portion 30 holding the main liquid plug PLm therein flow into the liquid holding portion 30 without flowing into the gas bypass channel portion 40, and so that the gases Gu1, Gu2, and Gu3 flowing through the upstream channel portion 10 toward the liquid holding portion 30 holding the main liquid plug PLm therein flow into the gas bypass channel portion 40 without flowing into the liquid holding portion 30.

Specifically, in the device 1, for example, the upstream liquid plugs PLu1 and PLu2 flowing through the upstream channel portion 10 toward the liquid holding portion 30 holding the main liquid plug PLm flow into the liquid holding portion 30 without flowing into the gas bypass channel portion 40 in a state in which the downstream end portion 42 of the gas bypass channel portion 40 is open, whereas the gases Gu1, Gu2, and Gu3 flowing through the upstream channel portion 10 toward the liquid holding portion 30 holding the main liquid plug PLm flow into the gas bypass channel portion 40 without flowing into the liquid holding portion 30 in a state in which the downstream end portion 32 of the liquid holding portion 30 is open.

A method of achieving the selective flow of the upstream liquid plugs PLu1, PLu2, and PLu3 into the liquid holding portion 30 and the selective flow of the gases Gu1, Gu2, and Gu3 into the gas bypass channel portion 40 is not particularly limited. For example, the upstream channel portion 10, the liquid holding portion 30, and the gas bypass channel portion 40 may be provided so that a change in free energy caused when the upstream liquid plugs PLu1 and PLu2 flow from the upstream channel portion 10 into the gas bypass channel portion 40 becomes larger than a change in free energy caused when the upstream liquid plugs PLu1 and PLu2 flow from the upstream channel portion 10 into the liquid holding portion 30 in a state in which the gas bypass channel portion 40 is filled with the gas Gb and the main liquid plug PLm is held in the liquid holding portion 30.

Specifically, for example, when the upstream end portion 41 of the gas bypass channel portion 40 is the enlarged channel (specifically, the sectional area of the upstream end portion 41 increases in the downstream direction) as illustrated in FIG. 1, FIG. 2A, and FIG. 2B, the upstream channel portion 10, the liquid holding portion 30, and the gas bypass channel portion 40 may be provided so that a contact angle of an inner surface 41a of the upstream end portion 41 with respect to the liquid that forms the upstream liquid plugs PLu1 and PLu2 in the gas (specifically, the gases Gu1, Gu2, and Gu3 flowing through the upstream channel portion 10 and the gas Gb in the gas bypass channel portion 40) is 90 degrees or larger, and so that an increase rate of an area of a gas-liquid interface, in a case where the upstream liquid plugs PLu1 and PLu2 flow from the downstream end portion 11 of the upstream channel portion 10 into the gas bypass channel portion 40, is larger than an increase rate of the area of the gas-liquid interface in a case where the upstream liquid plugs PLu1 and PLu2 flow from the downstream end portion 11 of the upstream channel portion 10 into the liquid holding portion 30.

In this case, the increase rate of the area of the gas-liquid interface in the case where the upstream liquid plugs PLu1 and PLu2 flow from the downstream end portion 11 of the upstream channel portion 10 into the liquid holding portion 30 is a ratio of the area of the gas-liquid interface in a state in which the upstream liquid plugs PLu1 and PLu2 are held in the upstream end portion 31 of the liquid holding portion 30 with respect to the area of the gas-liquid interface in a state in which the upstream liquid plugs PLu1 and PLu2 are held in the downstream end portion 11.

Further, the increase rate of the area of the gas-liquid interface in the case where the upstream liquid plugs PLu1 and PLu2 flow from the downstream end portion 11 of the upstream channel portion 10 into the gas bypass channel portion 40 is a ratio of the area of the gas-liquid interface in a state in which the upstream liquid plugs PLu1 and PLu2 are held in the upstream end portion 41 of the gas bypass channel portion 40 with respect to the area of the gas-liquid interface in a state in which the upstream liquid plugs PLu1 and PLu2 are held in the downstream end portion 11.

In a case where the upstream end portion 41 of the gas bypass channel portion 40 is not the enlarged channel (for example, the sectional area of the upstream end portion 41 is constant in the downstream direction), the upstream channel portion 10, the liquid holding portion 30, and the gas bypass channel portion 40 may be provided so that the contact angle of the inner surface 41a of the upstream end portion 41 with respect to the liquid that forms the upstream liquid plugs PLu1 and PLu2 in the gas (specifically, the gases Gu1, Gu2, and Gu3 flowing through the upstream channel portion 10 and the gas Gb in the gas bypass channel portion 40) is 90 degrees or larger, and a wetted side length in a case where the upstream liquid plugs PLu1 and PLu2 flow from the downstream end portion 11 of the upstream channel portion 10 into the liquid holding portion 30 is larger than a wetted side length in a case where the upstream liquid plugs PLu1 and PLu2 flow from the downstream end portion 11 of the upstream channel portion 10 into the gas bypass channel portion 40.

In this case, the wetted side length in the case where the upstream liquid plugs PLu1 and PLu2 flow from the downstream end portion 11 of the upstream channel portion 10 into the liquid holding portion 30 is $2 \times W1 \times H1$ (µm²) when, for example, a sectional shape of an uppermost-stream side portion of the upstream end portion 31 of the liquid holding portion 30 is rectangular with a width W1 (µm) and a height H1 (µm).

Further, the wetted side length in the case where the upstream liquid plugs PLu1 and PLu2 flow from the downstream end portion 11 of the upstream channel portion 10 into the gas bypass channel portion 40 is 2×W2×H2 ($\mu m^2$) when, for example, a sectional shape of an uppermost-stream side portion of the upstream end portion 41 of the gas bypass channel portion 40 is rectangular with a width W2 ($\mu m$) and a height H2 ($\mu m$).

Further, the above-mentioned contact angle of the inner surface 41a of the upstream end portion 41 of the gas bypass channel portion 40 with respect to the liquid that forms the upstream liquid plugs PLu1 and PLu2 is not particularly limited as long as the contact angle is 90 degrees or larger and smaller than 180 degrees, and may be, for example, 100 degrees or larger.

A method of adjusting the contact angle of the inner surface 41a of the upstream end portion 41 of the gas bypass channel portion 40 with respect to the liquid is not particularly limited. The contact angle may be adjusted by, for example, changing a combination of the liquid that forms the upstream liquid plugs PLu1 and PLu2, the gases Gu1, Gu2, and Gu3 flowing through the upstream channel portion 10 and the gas Gb in the gas bypass channel portion 40, and the material that forms the inner surface 41a.

Specifically, for example, in a case where the gas bypass channel portion 40 is formed by forming a groove on the surface of the substrate, the contact angle of the inner surface 41a with respect to the liquid may be adjusted within the above-mentioned range by the selection of the material that forms the substrate and/or a hydrophobization treatment on the inner surface 41a of the upstream end portion 41 of the gas bypass channel portion 40.

In the above-mentioned item (b) of the method, the gas bypass channel portion 40 is filled with the gas Gb, while the main liquid plug PLm is held in the liquid holding portion 30. Specifically, as illustrated in part (i) of FIG. 2A, the gas is held in the downstream end portion 11 of the upstream channel portion 10, the gas bypass channel portion 40, and the upstream end portion 21 of the downstream channel portion 20, while the liquid is held in the liquid holding portion 30 between the downstream end portion 11 of the upstream channel portion 10 and the upstream end portion 21 of the downstream channel portion 20. Specifically, the main liquid plug PLm is a liquid plug sandwiched between a gas held in the downstream end portion 11 of the upstream channel portion 10 and a gas held in the upstream end portion 21 of the downstream channel portion 20.

In this case, a method of filling the gas bypass channel portion 40 with the gas Gb and holding the main liquid plug PLm in the liquid holding portion 30 is not particularly limited. For example, a method including a manipulation illustrated in FIG. 3A and FIG. 3B may be used.

Figure 3A:
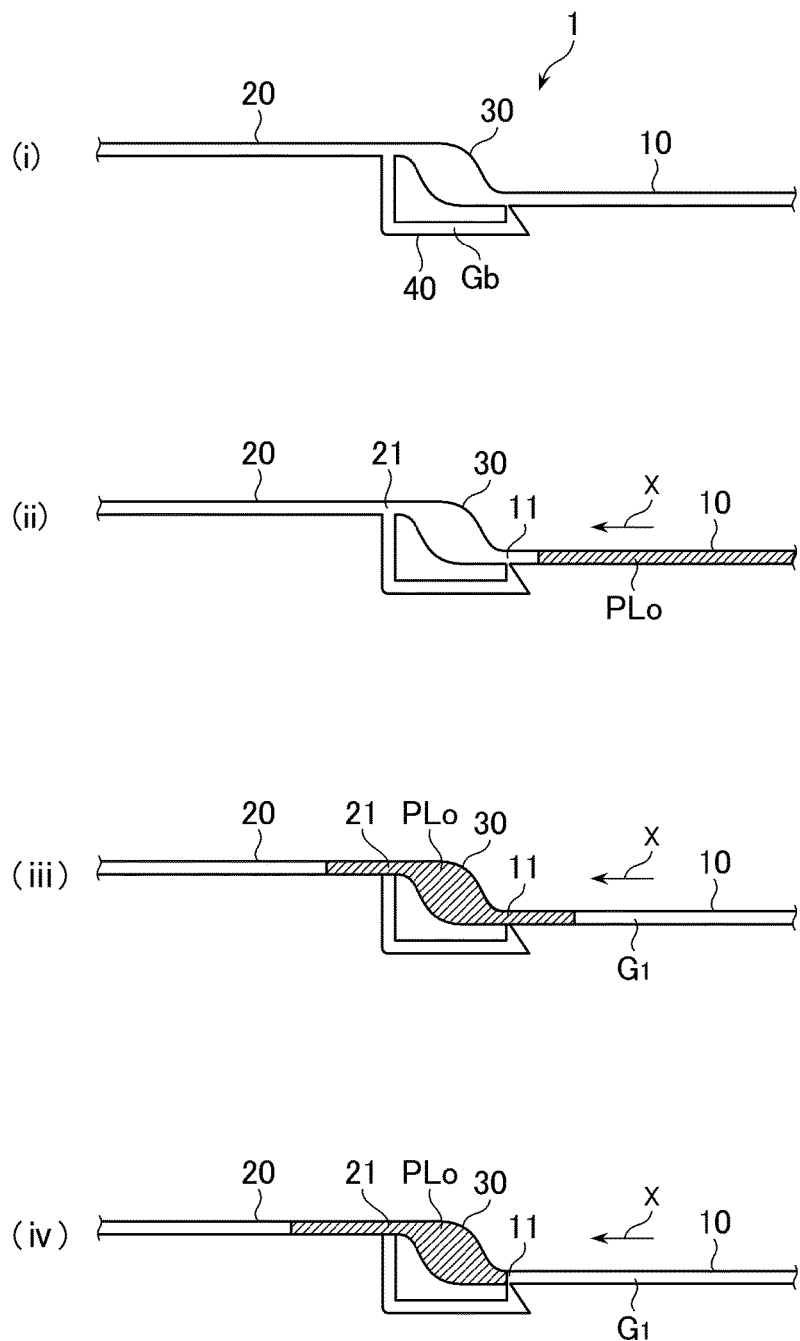
FIG. 3A is an explanatory view for illustrating a part of a manipulation involved in another example of the method according to the embodiment of the present invention.

Specifically, as illustrated in FIG. 3A and FIG. 3B, in the above-mentioned item (b), the following (b1) to (b5) may be sequentially implemented to fill the gas bypass channel portion 40 with the gas Gb and hold the main liquid plug PLm in the liquid holding portion 30: (b1) filling the upstream channel portion 10, the downstream channel portion 20, the liquid holding portion 30, and the gas bypass channel portion 40 with the gas (part (i) of FIG. 3A); (b2) causing a liquid plug PLo having a larger volume than a volume of the liquid holding portion 30 to flow through the upstream channel portion 10 toward the liquid holding portion 30 (part (ii) of FIG. 3A); (b3) causing the liquid plug PLo to flow into the liquid holding portion 30 without allowing the liquid plug to flow into the gas bypass channel portion 40 to be held in the downstream end portion 11 of the upstream channel portion 10, the liquid holding portion 30, and the upstream end portion 21 of the downstream channel portion 20 (part (iii) of FIG. 3A); (b4) causing a gas G1 following the liquid plug PLo to flow from the downstream end portion 11 of the upstream channel portion 10 into the gas bypass channel portion 40 without allowing the gas to flow into the liquid holding portion 30 to push out apart of the gas Gb in the gas bypass channel portion 40 to the upstream end portion 21 of the downstream channel portion 20, to thereby cut a portion of the liquid plug PLo, which is held in the upstream end portion 21 of the downstream channel portion 20, to form a downstream liquid plug PLd0 (part (iv) of FIG. 3A and part (v) of FIG. 3B); and (b5) causing the downstream liquid plug PLd0 in the downstream channel portion 20 to further flow in the downstream direction (part (vi) of FIG. 3B and part (vii) of FIG. 3B).

In the above-mentioned item (c) of the method, the first upstream liquid plug PLu1 and the second upstream liquid plug PLu2 are sequentially caused to flow through the upstream channel portion toward the liquid holding portion 30. Specifically, as illustrated in part (ii) of FIG. 2A, the first upstream liquid plug PLu1 sandwiched between the gas Gu1 on the downstream side and the gas Gu2 on the upstream side and the second upstream liquid plug PLu2 sandwiched between the gas Gu2 on the downstream side and the gas Gu3 on the upstream side on the downstream side of the first upstream liquid plug PLu1 are sequentially caused to flow.

A volume of the first upstream liquid plug PLu1 and a volume of the second upstream liquid plug PLu2 are not particularly limited as long as a part of the main liquid plug PLm, which is pushed out to the downstream channel portion 20 in the above-mentioned item (d) and the above-mentioned item (f), fills the upstream end portion 21 of the downstream channel portion 20 (specifically, the part closes the opening of the downstream end portion 42 of the gas bypass channel portion 40 at the upstream end portion 21), and, for example, may be equal to or smaller than the volume of the main liquid plug PLm held in the liquid holding portion 30 or may be smaller than the volume of the main liquid plug PLm.

Further, each of the volumes of the first upstream liquid plug PLu1 and the second upstream liquid plug PLu2 may be, for example, smaller than 1 $\mu L$, may be equal to or smaller than 500 nL, or may be equal to or smaller than 200 nL. Further, each of the volume of the first upstream liquid plug PLu1 and the volume of the second upstream liquid plug PLu2 may be set to, for example, 1 nL or larger.

Further, in the above-mentioned item (c), the first upstream liquid plug PLu1 and the second upstream liquid plug PLu2 may be caused to flow so that the second downstream liquid plug PLd2 is formed in the above-mentioned item (g) within a time shorter than 1 second after the formation of the first downstream liquid plug PLd1 in the above-mentioned item (e).

In this case, a plurality of samplings are achieved at time intervals shorter than 1 second. The above-mentioned time interval may be set to, for example, 500 milliseconds or shorter. The above-mentioned time interval may be set to, for example, 1 millisecond or longer.

The time intervals for forming the plurality of downstream liquid plugs PLd1 and PLd2 may be adjusted within the above-mentioned range by adjusting one or more selected from the group consisting of, for example, the volume of the gas Gu2 sandwiched between the first upstream liquid plug PLu1 and the second upstream liquid plug PLu2, the volume of the second upstream liquid plug PLu2, and a flow velocity of the second upstream liquid plug PLu2.

Further, in the above-mentioned item (c), the first upstream liquid plug PLu1 and the second upstream liquid plug PLu2 may be caused to flow so that the second upstream liquid plug PLu2 is merged with the main liquid plug PLm in the above-mentioned item (f) within a time shorter than 1 second after the first upstream liquid plug PLu1 is merged with the main liquid plug PLm in the above-mentioned item (d).

In this case, the merging of the plurality of upstream liquid plugs PLu1 and PLu2 and the main liquid plug PLm within the time intervals shorter than 1 second is achieved. The time interval may be set to, for example, 500 milliseconds or shorter. The time interval may be set to, for example, 1 millisecond or longer.

The time intervals that allow the plurality of upstream liquid plugs PLu1 and PLu2 and the main liquid plug PLm to be merged with each other may be adjusted within the above-mentioned range by adjusting one or more selected from the group consisting of, for example, the volume of the first upstream liquid plug PLu1, the volume of the gas Gu2 sandwiched between the first upstream liquid plug PLu1 and the second upstream liquid plug PLu2, and the flow velocity of the upstream liquid plugs PLu1 and PLu2.

A method of causing the first upstream liquid plug PLu1 and the second upstream liquid plug PLu2 to flow through the upstream channel portion 10 is not particularly limited. The first upstream liquid plug PLu1 and the second upstream liquid plug PLu2 may be caused to flow, for example, by applying a pressure to the first upstream liquid plug PLu1 and the second upstream liquid plug PLu2 on the upstream side, or may be caused to flow by reducing a pressure on the downstream side.

In the above-mentioned item (c), the number of liquid plugs to be caused to flow through the upstream channel portion 10 is not limited as long as the number is two or larger. Therefore, three or more liquid plugs may be caused to flow. Specifically, in the above-mentioned item (c), a plurality of upstream liquid plugs arranged so as to be separated from each other by a gas therebetween may be caused to flow.

In the above-mentioned item (d) of the method, the first upstream liquid plug PLu1 is caused to flow into the liquid holding portion 30. In this manner, the first upstream liquid plug PLu1 is merged with the main liquid plug PLm, while a part of the main liquid plug PLm after the merging is pushed out to the downstream channel portion 20.

Specifically, firstly, as illustrated in part (iii) of FIG. 2A, the first upstream liquid plug PLu1 is caused to flow into the liquid holding portion 30 without allowing the first upstream liquid plug to flow into the gas bypass channel portion 40. In this manner, the first upstream liquid plug PLu1 is merged with the main liquid plug PLm.

Next, as illustrated in part (iv) of FIG. 2A, the gas Gu2 following the first upstream liquid plug PLu1 is caused to flow to the downstream end portion 11 of the upstream channel portion 10, thereby pushing out a part of the main liquid plug PLm to a downstream side of the upstream end portion 21 of the downstream channel portion 20.

At this time, a volume of a part of the main liquid plug PLm pushed out from the liquid holding portion 30 is the same as the volume of the first upstream liquid plug PLu1. Further, the volume of the main liquid plug PLm after the merging is equal to the sum of the volume of the main liquid plug PLm before the merging and the volume of the first upstream liquid plug PLu1.

The liquid that forms the first upstream liquid plug PLu1 and the liquid that forms the main liquid plug PLm are mixed with each other by the merging of the first upstream liquid plug PLu1 and the main liquid plug PLm.

In the above-mentioned item (e) of the method, the gas Gu2 following the first upstream liquid plug PLu1 is caused to flow into the gas bypass channel portion 40 to push out a part of the gas Gb in the gas bypass channel portion 40 to the upstream end portion 21 of the downstream channel portion 20. As a result, the part of the main liquid plug PLm, which is pushed out in the above-mentioned item (d), is cut to form the first downstream liquid plug PLd1.

Specifically, as illustrated in part (v) of FIG. 2A, the gas Gu2 following the first upstream liquid plug PLu1 is caused to flow into the gas bypass channel portion 40 without allowing the gas Gu2 to flow into the liquid holding portion 30, thereby pushing out the part of the gas Gb held in the gas bypass channel portion 40 to the upstream end portion 21 of the downstream channel portion 20.

As a result, the part of the main liquid plug PLm (see part (iv) of FIG. 2A), which has been pushed out to the downstream channel portion 20 in the above-mentioned item (d), is separated away from the remaining portion held in the liquid holding portion 30 to form the first downstream liquid plug PLd1.

A volume of the first downstream liquid plug PLd1 is the same as the volume of the first upstream liquid plug PLu1. Specifically, for example, when the volume of the first upstream liquid plug PLu1 is smaller than 1 µL as described above, the volume of the first downstream liquid plug PLd1 is also smaller than 1 µL and is the same as the volume of the first upstream liquid plug PLu1.

In the above-mentioned item (f) of the method, the second upstream liquid plug PLu2 is caused to flow into the liquid holding portion 30. In this manner, the second upstream liquid plug PLu2 is merged with the main liquid plug PLm, while a part of the main liquid plug PLm after the merging is pushed out to the downstream channel portion 20.

Specifically, as in the case of the first upstream liquid plug PLu1 described above, firstly, as illustrated in part (vi) of FIG. 2B, the second upstream liquid plug PLu2 is caused to flow into the liquid holding portion 30 without allowing the second upstream liquid plug to flow into the gas bypass channel portion 40. In this manner, the second upstream liquid plug PLu2 is merged with the main liquid plug PLm.

Next, as illustrated in part (vii) of FIG. 2B, the gas Gu3 following the second upstream liquid plug PLu2 is caused to flow to the downstream end portion 11 of the upstream channel portion 10, thereby pushing out a part of the main liquid plug PLm to a downstream side of the upstream end portion 21 of the downstream channel portion 20.

At this time, a volume of a part of the main liquid plug PLm pushed out from the liquid holding portion 30 is the same as the volume of the second upstream liquid plug PLu2. Further, the volume of the main liquid plug PLm after the merging is equal to the sum of the volume of the main liquid plug PLm before the merging and the volume of the second upstream liquid PLu2.

The liquid that forms the second upstream liquid plug PLu2 and the liquid that forms the main liquid plug PLm are mixed with each other by the merging of the second upstream liquid plug PLu2 and the main liquid plug PLm.

Specifically, through the merging of the second upstream liquid plug PLu2 and the main liquid plug PLm, the liquid that forms the main liquid plug PLm before being merged with the first upstream liquid plug PLu1, the liquid that forms the first upstream liquid plug PLu1, and the liquid that forms the second upstream liquid plug PLu2, are mixed with each other.

Further, as described above, the merging of the second upstream liquid plug PLu2 and the main liquid plug PLm may be carried out within a time shorter than 1 second after the first upstream liquid plug PLu1 is merged with the main liquid plug PLm in the above-mentioned item (d).

In the above-mentioned item (g) of the method, the gas Gu3 following the second upstream liquid plug PLu2 is caused to flow into the gas bypass channel portion 40 to push out a part of the gas Gb in the gas bypass channel portion 40 to the upstream end portion 21 of the downstream channel portion 20. As a result, the part of the main liquid plug PLm, which has been pushed out in the above-mentioned item (f), is cut to form the second downstream liquid plug PLd2.

Specifically, as in the case of the first downstream liquid plug PLd1 described above, as illustrated in part (viii) of FIG. 2B, the gas Gu3 following the second upstream liquid plug PLu2 is caused to flow into the gas bypass channel portion 40 without allowing the gas Gu3 to flow into the liquid holding portion 30, thereby pushing out the part of the gas Gb held in the gas bypass channel portion 40 to the upstream end portion 21 of the downstream channel portion 20.

As a result, the part of the main liquid plug PLm (see part (vii) of FIG. 2B), which has been pushed out to the downstream channel portion 20 in the above-mentioned item (f), is separated away from the remaining portion held in the liquid holding portion 30 to form the second downstream liquid plug PLd2.

A volume of the second downstream liquid plug PLd2 is the same as the volume of the second upstream liquid plug PLu2. Specifically, for example, when the volume of the second upstream liquid plug PLu2 is smaller than 1 μL as described above, the volume of the second downstream liquid plug PLd2 is also smaller than 1 μL and is the same as the volume of the second upstream liquid plug PLu2.

Further, as described above, the second downstream liquid plug PLd2 may be formed within a time shorter than 1 second after the formation of the first downstream liquid plug PLd1 in the above-mentioned item (e). In this case, as described above, the formation of the plurality of downstream liquid plugs PLd1 and PLd2 is achieved at time intervals shorter than 1 second.

According to the device and the method described above, an effective manipulation of the tiny amount of liquid is achieved in the microchannel device. Specifically, in particular, the device 1 including the gas bypass channel portion 40 is used to sequentially merge the plurality of upstream liquid plugs PLu1 and PLu2 with the main liquid plug PLm in an intermittent manner, while the gases Gu2 and Gu3 respectively following the plurality of upstream liquid plugs PLu1 and PLu2 are caused to take a detour from the upstream channel portion 10 to the downstream channel portion 20 without flowing into the liquid holding portion 30. As a result, the plurality of downstream liquid plugs PLd1 and PLd2 corresponding to the plurality of upstream liquid plugs PLu1 and PLu2 are sequentially formed in an intermittent manner to keep the volume of the main liquid plug PLm constant.

Further, for example, by adjusting conditions for causing the plurality of upstream liquid plugs PLu1 and PLu2 to flow in the upstream channel portion 10 as described above, the second upstream liquid plug PLu2 is also merged with the main liquid plug PLm in the above-mentioned item (f) within a time shorter than 1 second after the merging of the first upstream liquid plug PLu1 with the main liquid plug PLm in the above-mentioned item (d).

In this case, the merging of the upstream liquid plugs PLu1 and PLu2 with the main liquid plug PLm (specifically, the mixture of the liquid that forms the upstream liquid plugs PLu1 and PLu2 and the liquid that forms the main liquid plug PLm) the plurality of times is performed with extremely high temporal resolution.

Further, according to the device 1 and the method described above, effective sampling is achieved in the microchannel device. Specifically, in particular, the device 1 including the gas bypass channel portion 40 is used to cause the gases Gu2 and Gu3 respectively following the plurality of upstream liquid plugs PLu1 and PLu2 to take a detour from the upstream channel portion 10 to the downstream channel portion 20 without allowing the gases Gu2 and Gu3 to flow into the liquid holding portion 30. As a result, the plurality of downstream liquid plugs PLd1 and PLd2 are formed as the plurality of intermittent samplings at desired time intervals.

More specifically, for example, the second downstream liquid plug PLd2 may be formed within the time shorter than 1 second after the formation of the first downstream liquid plug PLd1 in the above-mentioned item (e) as described above. Specifically, by adjusting the conditions for causing the plurality of upstream liquid plugs PLu1 and PLu2 to flow in the upstream channel portion 10, the second downstream liquid plug PLd2 is formed in the above-mentioned item (g) within the time shorter than 1 second after the formation of the first downstream liquid plug PLd1 in the above-mentioned item (e). In this case, the plurality of samplings at the time intervals shorter than 1 second are achieved. In other words, the plurality of samplings are carried out with extremely high temporal resolution.

Further, for example, when each of the volumes of the first upstream liquid plug PLu1, the second upstream liquid plug PLu2, the first downstream liquid plug PLd1, and the second downstream liquid plug PLd2 is smaller than 1 μL as described above, an effective manipulation of an infinitesimal amount of liquid is achieved.

The method may further include the following (h): (h) recovering the first downstream liquid plug PLd1 and the second downstream liquid plug PLd2. In this case, in the above-mentioned item (h) of the method, the first downstream liquid plug PLd1 and the second downstream liquid plug PLd2 are recovered. Specifically, as illustrated in part (ix) of FIG. 2B and part (x) of FIG. 2B, the first downstream liquid plug PLd1 and the second downstream liquid plug PLd2 formed as described above are recovered from the downstream channel portion 20. Further, in the above-mentioned item (h), the recovered first downstream liquid plug PLd1 and second downstream liquid plug PLd2 may be analyzed.

In the method, the main liquid plug PLm held in the liquid holding portion 30 in the item (b) may contain a first factor, and one or both of the first upstream liquid plug PLu1 and the second upstream liquid plug PLu2 that are caused to flow through the upstream channel portion in the item (d) may contain a second factor which acts on the first factor.

In this case, the upstream liquid plugs PLu1 and PLu2 are merged with the main liquid plug PLm in the above-mentioned item (d) and/or the above-mentioned item (f). As a result, it is made possible for the second factor to act on the first factor. The first factor may be fixed to the liquid holding portion 30.

Further, the second factor may directly act on the first factor or may indirectly act on the first factor in the main liquid plug PLm. The indirect action of the second factor on the first factor may be achieved, for example, firstly by generation of a third factor from the second factor and then by action of the third factor on the first factor in the main liquid plug PLm.

Specifically, for example, the first factor may be a cell body, and the second factor may be a substance to act on the cell body (such as a stimulating substance). In this case, the cell body may be fixed to the liquid holding portion 30.

The cell body is not particularly limited, and may be, for example, an animal cell. The animal cell may be, for example, a mammal cell. Specifically, the animal cell may be, for example, a human cell or a cell of an animal other than a human (for example, monkey, pig, dog, rat, or mouse). Further, the animal cell may be a primary cell obtained from a human or an animal other than a human, or may be an established cell line. Further, the animal cell may be a differentiated cell or an undifferentiated cell. Further, the animal cell may be an embryonic stem cell or a cell derived therefrom, or may be an iPS (induced pluripotent stem) cell or a cell derived therefrom. Further, the cell body may be an animal cell other than a mammal cell. Further, the cell body may be, for example, a microbe. Further, the cell body may be, for example, a plant cell.

The device 1 and the method manipulate the infinitesimal amount of liquid as described above. Therefore, for example, the plurality of upstream liquid plugs PLu1 and PLu2, each formed of an infinitesimal amount of liquid containing a scarce stimulating substance, are sequentially merged with the tiny amount of the main liquid plug PLm containing a few scarce cell bodies in an intermittent manner, while the plurality of downstream liquid plugs PLd1 and PLd2 respectively corresponding to the plurality of upstream liquid plugs PLu1 and PLu2 are sequentially formed in an intermittent manner. In this manner, a concentration of the stimulating substance contained in the main liquid plug PLm is increased in a stepwise manner, while the volume of the main liquid plug PLm is kept constant. As a result, a change in culture environment for the cell body is controlled with high accuracy.

Further, the device 1 and the method achieve the plurality of effective samplings by sequentially forming the plurality of downstream liquid plugs PLd1 and PLd2 respectively corresponding to the plurality of upstream liquid plugs PLu1 and PLu2 in an intermittent manner, as described above. Therefore, for example, a response of the few scarce cell bodies contained in the main liquid plug PLm to the stimulating substance is effectively evaluated.

Specifically, for example, the main liquid plug PLm held in the liquid holding portion 30 in the above-mentioned item (b) may contain the cell body, whereas one or both of the first upstream liquid plug PLu1 and the second upstream liquid plug PLu2 that are caused to flow through the upstream channel portion 10 in the above-mentioned item (c) may contain the stimulating substance that changes a quantity of secretion from the cell body (quantity of a specific substance secreted from the cell body) and/or velocity of the secretion (velocity at which the cell body secretes the specific substance).

More specifically, for example, the cell body contained in the main liquid plug PLm held in the liquid holding portion 30 in the above-mentioned item (b) is a Langerhans cell, and one or both of the first upstream liquid plug PLu1 and the second upstream liquid plug PLu2 that are caused to flow through the upstream channel portion 10 may contain glucose in the above-mentioned item (c).

In this case, the specific substance secreted from the Langerhans cell is insulin, and glucose is a stimulating substance that changes the secretion quantity and/or the secretion velocity of insulin from the Langerhans cell.

Then, in a case where the main liquid plug PLm held in the liquid holding portion 30 contains the cell body in the above-mentioned item (b) and one or both of the first upstream liquid plug PLu1 and the second upstream liquid plug PLu2 that are caused to flow through the upstream channel portion 10 contain the stimulating substance that changes the quantity and/or the velocity of the secretion from the cell body in the above-mentioned item (c), the upstream liquid plugs PLu1 and PLu2 are merged with the main liquid plug PLm in the above-mentioned item (d) and/or the above-mentioned item (f) to allow the stimulating substance to act on the cell body in the liquid holding portion 30. As a result, in the above-mentioned item (e) and/or the above-mentioned item (g), the first downstream plug PLd1 and/or the second downstream plug PLd2 containing the specific substance secreted from the cell body at the quantity and/or the velocity changed by the action of the stimulating substance is formed.

Therefore, by recovering and analyzing the first downstream liquid plug PLd1 and/or the second downstream liquid plug PLd2 in the above-mentioned item (h), the response of the cell body to the stimulating substance is evaluated with the high temporal resolution as described above.

The response of the cell body to the stimulating substance may be evaluated without sampling. Specifically, for example, in the device 1 placed on a sample stage of a microscope, the plurality of upstream liquid plugs PLu1 and PLu2 containing the stimulating substance are merged with the main liquid plug PLm containing the cell body, while the plurality of downstream liquid plugs PLd1 and PLd2 are formed. As a result, the response of the cell body to the stimulating substance is observed under the microscope and evaluated.

Further, the first factor is not limited to the cell body. Specifically, for example, the first factor may be a first substance, while the second factor may be a second substance that generates a third substance through interaction with the first substance.

Specifically, for example, the first factor is an enzyme fixed to the liquid holding portion 30, whereas the second factor may be a substrate for the enzyme. In this case, the upstream liquid plugs PLu1 and PLu2 containing the substrate are merged with the main liquid plug PLm containing the enzyme in the above-mentioned item (d) and/or the above-mentioned item (f) to bring the substrate into contact with the enzyme in the liquid holding portion 30 to cause an enzyme reaction. In the above-mentioned item (e) and/or the above-mentioned item (g), the first downstream liquid plug PLd1 and/or the second downstream liquid plug PLd2, each containing a product generated by the enzyme reaction, is formed.

Therefore, by recovering and analyzing the first downstream liquid plug PLd1 and/or the second downstream liquid plug PLd2 in the above-mentioned item (h), the amount of products generated by the enzyme reaction and an enzyme reaction velocity are evaluated with the high temporal resolution described above.

Figure 4:
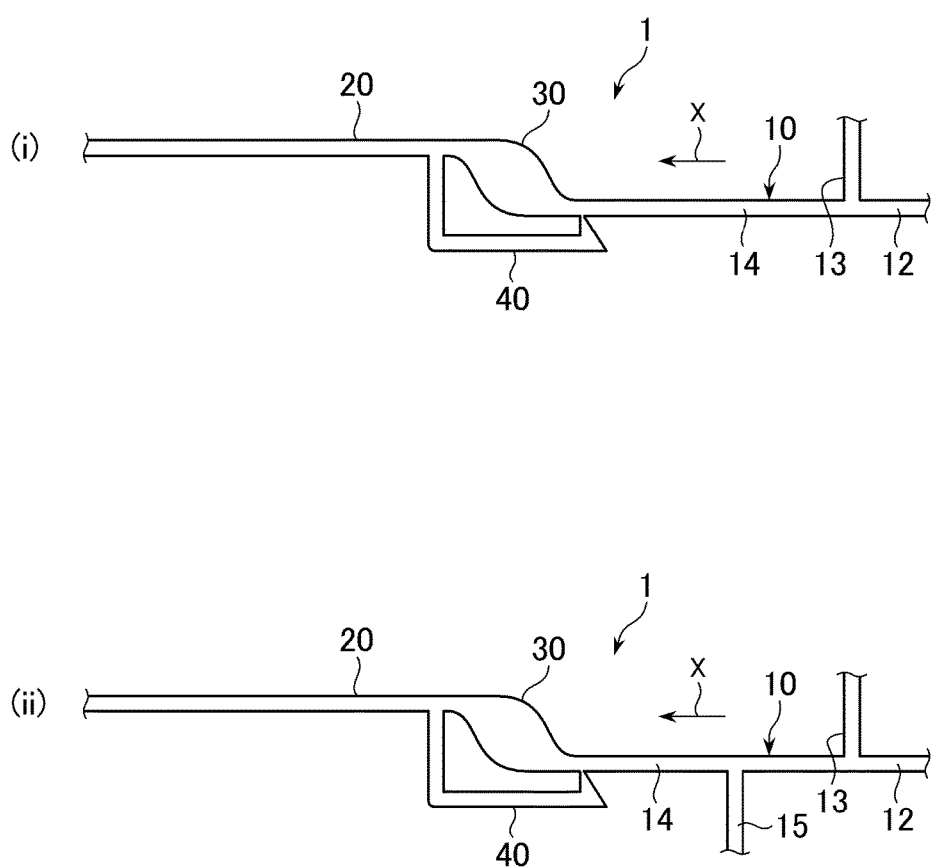
FIG. 4 is an explanatory view for illustrating another example of the microchannel device according to the embodiment of the present invention.

In FIG. 4, another example of the device 1 is illustrated. In the example illustrated in part (i) of FIG. 4, the upstream channel portion 10 of the device 1 includes a liquid supply portion 12 for supplying the liquid that forms the upstream liquid plugs PLu1 and PLu2 (see FIG. 2A), a gas supply portion 13 for supplying a gas for cutting the liquid to form the upstream liquid plugs PLu1 and PLu2, and a merged channel portion 14 for allowing the formed upstream liquid plugs PLu1 and PLu2 to flow toward the liquid holding portion 30. The upstream channel portion 10 includes the liquid supply portion 12 and the gas supply portion 13. As a result, the plurality of upstream liquid plugs PLu1 and PLu2 are efficiently formed in the upstream channel portion 10.

In the example illustrated in part (ii) of FIG. 4, the upstream channel portion 10 of the device 1 includes the liquid supply portion 12, the gas supply portion 13, a composition adjusting portion 15 provided downstream of the liquid supply portion 12 and the gas supply portion 13, for adding the factor to the upstream liquid plugs PLu1 and PLu2 to adjust a composition of the upstream liquid plugs PLu1 and PLu2, and the merged channel portion 14 for allowing the upstream liquid plugs PLu1 and PLu2 whose composition is adjusted to flow toward the liquid holding portion 30. The upstream channel portion 10 further includes the composition adjusting portion 15. As a result, the plurality of upstream liquid plugs PLu1 and PLu2 whose composition is adjusted are efficiently formed in the upstream channel portion 10.

Specifically, for example, in a case where the main liquid plug PLm held in the liquid holding portion 30 contains the cell body in the above-mentioned item (b) as described above and one or both of the first upstream liquid plug PLu1 and the second upstream liquid plug PLu2 that are caused to flow through the upstream channel portion 10 contain the stimulating substance that changes the quantity and/or the velocity of the secretion from the cell body in the above-mentioned item (c), the upstream channel portion 10 includes the composition adjusting portion 15 for adding the stimulating substance to the first upstream liquid plug PLu1 and/or the second upstream liquid plug PLu2. As a result, the first upstream liquid plug PLu1 and the second upstream liquid plug PLu2 containing the stimulating substance at different concentrations are efficiently formed.

In FIG. 5, further examples of the device 1 are illustrated. In the example illustrated in part (i) of FIG. 5, the gas bypass channel portion 40 includes the upstream end portion 41 that is not the enlarged channel. Specifically, in this example, the sectional area of the upstream end portion 41 of the gas bypass channel portion 40 is constant in the downstream direction of the gas bypass channel portion 40. Further, the sectional area of the opening of the upstream end portion 41 of the gas bypass channel portion 40 at the downstream end portion 11 of the upstream channel portion 10 is smaller than the sectional area of the downstream end portion 11 of the upstream channel portion 10.

In the example illustrated in part (ii) of FIG. 5, the gas bypass channel portion 40 includes the upstream end portion 41 including the enlarged channel that is shorter than that in the above-mentioned example illustrated in FIG. 1 to FIG. 4. Specifically, the upstream end portion 41 includes an enlarged channel portion that is open to the downstream end portion 11 of the upstream channel portion 10 and extends from the downstream end portion 11 in a direction approximately orthogonal to the flow direction and a portion having a constant sectional area, which extends in the downstream direction of the enlarged channel portion in the approximately orthogonal direction.

In the example illustrated in part (iii) of FIG. 5, this device includes the two gas bypass channel portions 40, 50. Specifically, in this example, the device 1 includes the first gas bypass channel portion 40 provided so as to bypass the liquid holding portion 30 from the downstream end portion 11 of the upstream channel portion 10 to the upstream end portion 21 of the downstream channel portion 20 on one side of the upstream channel portion 10, and a second gas bypass channel portion 50 provided so as to bypass the liquid holding portion 30 from the downstream end portion 11 of the upstream channel portion 10 to the upstream end portion 21 of the downstream channel portion 20 on another side of the upstream channel portion 10.

Next, a specific Example according to this embodiment is described.

EXAMPLE

[Manufacture of Microchannel Device]

Figure 6:
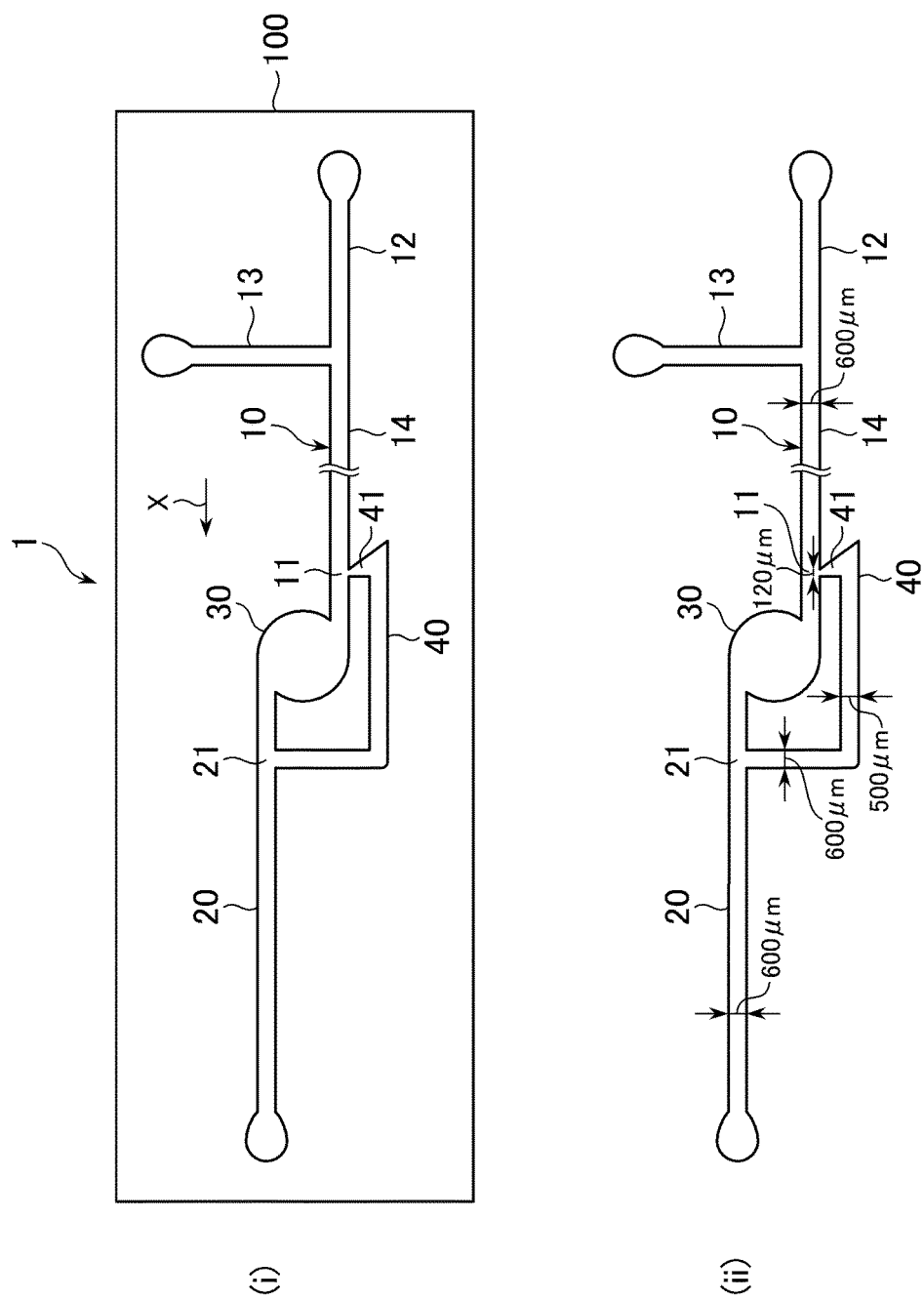
FIG. 6 is an explanatory view for illustrating a microchannel device used in the Example according to the embodiment of the present invention.

The device 1 as illustrated in FIG. 6 was manufactured by a microfabrication technology. Specifically, as illustrated in part (i) of FIG. 6, by replica molding using a photoresist, grooves to form the upstream channel portion 10 including the liquid supply portion 12, the gas supply portion 13, the downstream channel portion 20, the liquid holding portion 30, and the gas bypass channel portion 40 having the upstream end portion 41 that was the enlarged channel, were formed on a surface of a substrate 100 made of polydimethylsiloxane (PDMS) with a thickness of about 4 mm. Then, a substrate (not shown) made of polydimethylsiloxane (PDMS) with a thickness of about 2 mm was laminated and bonded onto the substrate 100 made of PDMS to obtain the device 1.

In part (ii) of FIG. 6, dimensions of the respective portions of the device 1 that was manufactured are shown. Specifically, a width of the merged channel portion 14 of the upstream channel portion 10 was 600 µm, a width of the opening (distal end portion of the enlarged channel, which has the smallest sectional area) of the upstream end portion 41 of the gas bypass channel portion 40 at the downstream end portion 11 of the upstream channel portion 10, was 120 µm, a width of the downstream end portion 42 of the gas bypass channel portion 40 was 600 µm, a width of a portion of the gas bypass channel portion 40 between the upstream end portion 41 and the downstream end portion 42 was 500 µm, and a width of the downstream channel portion 20 was 600 µm.

The liquid holding portion 30 was circular with a diameter of 2 mm. The height of each of the upstream channel portion 10, the downstream channel portion 20, the liquid holding portion 30, and the gas bypass channel portion 40 was 150 µm. Further, inner surfaces of the upstream channel portion 10, the downstream channel portion 20, the liquid holding portion 30, and the gas bypass channel portion 40 were subjected to a hydrophobization treatment through fluorine-based resin coating. As a result, the contact angle of the inner surfaces of the respective channels including the inner surface 41a of the upstream end portion 41 of the gas bypass channel portion 40 with respect to water was 120 degrees in air.

[Implementation of Method Using Microchannel Device]

The method was implemented using the device 1 manufactured as described above. As the liquid that formed the liquid plugs, water added with a pigment for increasing visibility was used. As the gas, air was used. Further, the liquid and the gas were caused to flow through the channels by applying a pressure on the upstream side.

Figure 7:
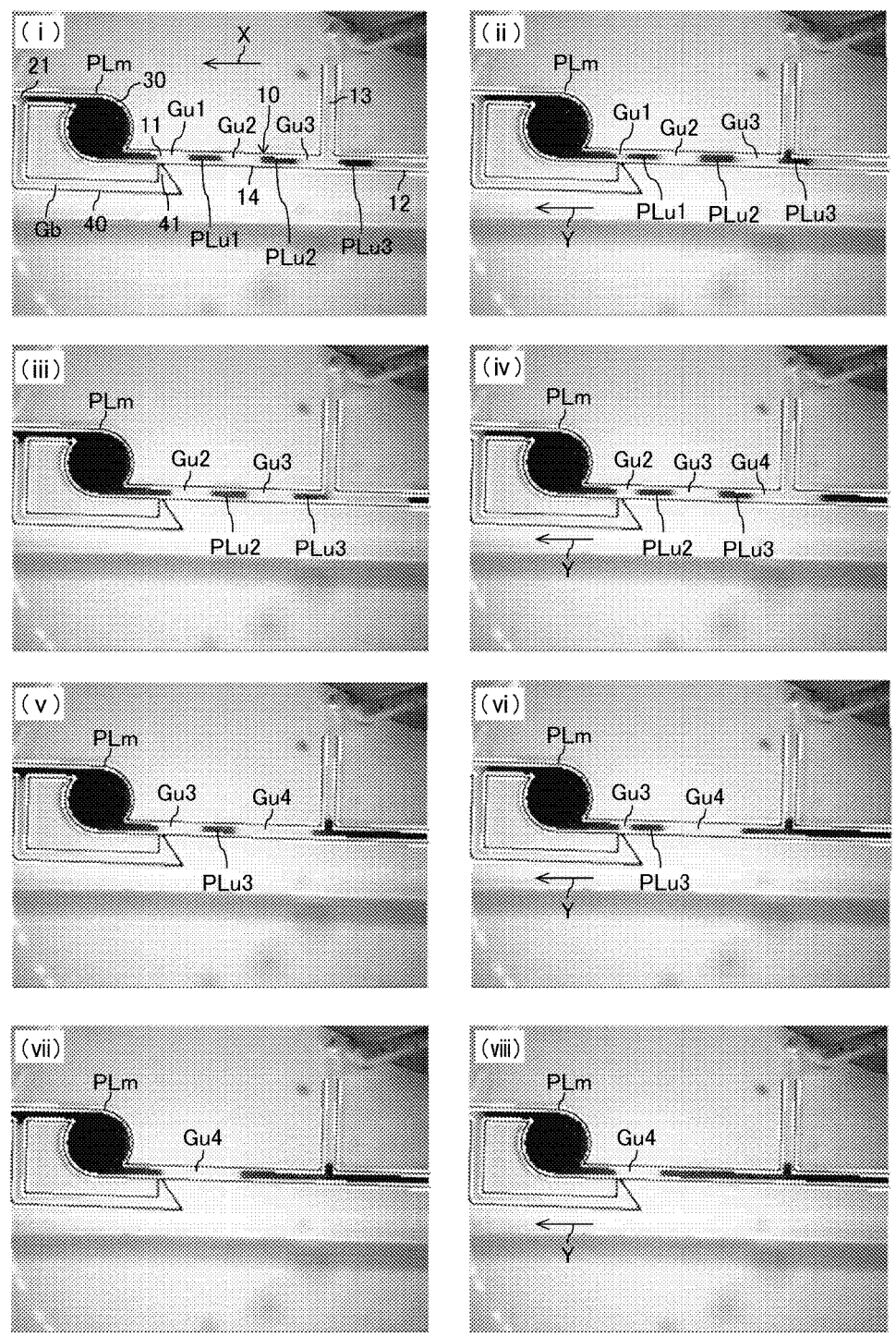
FIG. 7 is an explanatory view for showing an example of results of observation of flows of liquid plugs in the microchannel device in the Example according to the embodiment of the present invention.

In FIG. 7, the results of observation of the flow of the liquid plugs in the device 1 according to the method under a phase-contrast microscope are shown. Firstly, as shown in part (i) of FIG. 7 and part (ii) of FIG. 7, in a state in which the gas bypass channel portion 40 was filled with the gas Gb and the main liquid plug PLm was held in the liquid holding portion 30, the three liquid plugs PLu1, PLu2, and PLu3 were caused to sequentially flow through the upstream channel portion 10 toward the liquid holding portion 30. The volume of the main liquid plug PLm was about 1.5 µL. The volume of each of the three upstream liquid plugs PLu1, PLu2, and PLu3 was about 100 nL.

Next, as shown in part (iii) of FIG. 7, by causing the first upstream liquid plug PLu1 to flow into the liquid holding portion 30, the first upstream liquid plug PLu1 was merged with the main liquid plug PLm. Then, a part of the main liquid plug PLm after the merging was pushed out to the downstream channel portion 20.

Further, as shown in part (iv) of FIG. 7, the gas Gu2 following the first upstream liquid plug PLu1 was caused to flow into the gas bypass channel portion 40 to push out a part of the gas Gb in the gas bypass channel portion 40 to the upstream end portion 21 of the downstream channel portion 20, thereby cutting a part of the main liquid plug PLm, which had been pushed out to the downstream channel portion 20 as described above, and thus the first downstream liquid plug PLd1 was formed.

Next, as shown in part (v) of FIG. 7, by causing the second upstream liquid plug PLu2 to flow into the liquid holding portion 30, the second upstream liquid plug PLu2 was merged with the main liquid plug PLm. Then, a part of the main liquid plug PLm after the merging was pushed out to the downstream channel portion 20.

Further, as shown in part (vi) of FIG. 7, the gas Gu3 following the second upstream liquid plug PLu2 was caused to flow into the gas bypass channel portion 40 to push out a part of the gas Gb in the gas bypass channel portion 40 to the upstream end portion 21 of the downstream channel portion 20, thereby cutting a part of the main liquid plug PLm, which had been pushed out to the downstream channel portion 20 as described above, and thus the second downstream liquid plug PLd2 was formed.

Next, as shown in part (vii) of FIG. 7, by causing the third upstream liquid plug PLu3 to flow into the liquid holding portion 30, the third upstream liquid plug PLu3 was merged with the main liquid plug PLm. Then, a part of the main liquid plug PLm after the merging was pushed out to the downstream channel portion 20.

Further, as shown in part (viii) of FIG. 7, the gas Gu4 following the third upstream liquid plug PLu3 was caused to flow into the gas bypass channel portion 40 to push out a part of the gas Gb in the gas bypass channel portion 40 to the upstream end portion 21 of the downstream channel portion 20, thereby cutting a part of the main liquid plug PLm, which had been pushed out to the downstream channel portion 20 as described above, and thus the third downstream liquid plug PLd3 was formed. Then, the three downstream liquid plugs PLd1, PLd2, and PLd3 were recovered from the downstream channel portion 20.

According to the method described above, the three upstream liquid plugs PLu1, PLu2, and PLu3 were merged with the main liquid plug PLm in about 640 milliseconds, while the three downstream liquid plugs PLd1, PLd2, and PLd3 were formed in about 640 milliseconds.

Specifically, the merging of the plurality of the upstream liquid plugs PLu1, PLu2, and PLu3, and the main liquid plug PLm, and the formation (the plurality of samplings) of the plurality of downstream liquid plugs PLd1, PLd2, and PLd3, were successfully achieved with the temporal resolution of about 200 milliseconds.

REFERENCE SIGNS LIST 1 microchannel device, 10 upstream channel portion, 11 downstream end portion of upstream channel portion, 12 liquid supply portion, 13 gas supply portion, 14 merged channel portion, 15 composition adjusting portion, 20 downstream channel portion, 21 upstream end portion of downstream channel portion, 22 liquid supply portion, 23 gas supply portion, 24 plug composition adjusting portion, 30 liquid holding portion, 31 upstream end portion of liquid holding portion, 32 downstream end portion of liquid holding portion, 40, 50 gas bypass channel portion, 41, 51 upstream end portion of gas bypass channel portion, 41a inner surface of upstream end portion of gas bypass channel portion, 42 downstream end portion of gas bypass channel portion, 100 substrate

The invention claimed is:

1. A method, comprising the following (a) to (g):
   (a) providing a microchannel device comprising an upstream channel portion, a downstream channel portion, a liquid holding portion provided between a downstream end portion of the upstream channel portion and an upstream end portion of the downstream channel portion, and a gas bypass channel portion provided so as to bypass the liquid holding portion from the downstream end portion of the upstream channel portion to the upstream end portion of the downstream channel portion;
   (b) filling the gas bypass channel portion with a gas and holding a main liquid plug in the liquid holding portion;
   (c) causing a first upstream liquid plug and a second upstream liquid plug to sequentially flow through the upstream channel portion toward the liquid holding portion;
   (d) causing the first upstream liquid plug to flow into the liquid holding portion to merge the first upstream liquid plug with the main liquid plug, and pushing out a part of the main liquid plug after the merging to the downstream channel portion;
   (e) causing a gas in the upstream channel portion, which is following the first upstream liquid plug to flow into the gas bypass channel portion to push out a part of the gas in the gas bypass channel portion to the upstream end portion of the downstream channel portion, to thereby cut the part of the main liquid plug, which is pushed out in the item (d), to form a first downstream liquid plug;
   (f) causing the second upstream liquid plug to flow into the liquid holding portion to merge the second upstream liquid plug with the main liquid plug and pushing out a part of the main liquid plug after the merging to the downstream channel portion; and
   (g) causing a gas in the upstream channel portion, which is following the second upstream liquid plug to flow into the gas bypass channel portion to push out a part of the gas in the gas bypass channel portion to the upstream end portion of the downstream channel portion, to thereby cut the part of the main liquid plug, which is pushed out in the item (f), to form a second downstream liquid plug,
   wherein an upstream end portion of the gas bypass channel portion is open at the downstream end portion of the upstream channel portion, and the liquid holding portion is provided downstream of the upstream end portion of the gas bypass channel portion.

2. The method according to claim 1, further comprising the following (h):
   (h) recovering the first downstream liquid plug and the second downstream liquid plug.

3. The method according to claim 1, wherein the item (c) comprises causing the first upstream liquid plug and the second upstream liquid plug to flow so that the second downstream liquid plug is formed in the item (g) within a time shorter than 1 second after the formation of the first downstream liquid plug in the item (e).

4. The method according to claim 1, wherein the item (c) comprises causing the first upstream liquid plug and the second upstream liquid plug to flow so that the second upstream liquid plug is merged with the main liquid plug in the item (f) within a time shorter than 1 second after the first upstream liquid plug is merged with the main liquid plug in the item (d).

5. The method according to claim 1, wherein the volume of each of the first upstream liquid plug, the second upstream liquid plug, the first downstream liquid plug, and the second downstream liquid plug, is smaller than 1 µL.

6. The method according to claim 1, wherein:
the main liquid plug held in the liquid holding portion in the item (b) contains a first factor; and
one or both of the first upstream liquid plug and the second upstream liquid plug that is caused to flow through the upstream channel portion in the item (c) contain a second factor which directly or indirectly acts on the first factor.

7. The method according to claim 6, wherein:
the first factor is a cell body; and
the second factor is a substance which directly or indirectly acts on the cell body.

* * * * *